(12) United States Patent
Sowards et al.

(10) Patent No.: US 12,230,427 B2
(45) Date of Patent: Feb. 18, 2025

(54) MEDICAL-DEVICE MAGNETIZER SYSTEMS AND METHODS

(71) Applicant: Bard Access Systems, Inc., Salt Lake City, UT (US)

(72) Inventors: Steffan Sowards, Salt Lake City, UT (US); Anthony K. Misener, Bountiful, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 217 days.

(21) Appl. No.: 17/872,814

(22) Filed: Jul. 25, 2022

(65) Prior Publication Data

US 2023/0026443 A1 Jan. 26, 2023

Related U.S. Application Data

(60) Provisional application No. 63/225,793, filed on Jul. 26, 2021.

(51) Int. Cl.
*H01F 13/00* (2006.01)
*A61B 5/06* (2006.01)
*A61B 34/20* (2016.01)

(52) U.S. Cl.
CPC ........... *H01F 13/003* (2013.01); *A61B 34/20* (2016.02); *A61B 5/062* (2013.01)

(58) Field of Classification Search
CPC ....... H01F 13/003; A61B 34/20; A61B 5/062; A61B 90/98; A61B 2017/00876; A61B 2034/2051

(Continued)

(56) References Cited

U.S. PATENT DOCUMENTS 3,409,853 A 11/1968 Guerth
3,467,926 A 9/1969 Smith
(Continued)

FOREIGN PATENT DOCUMENTS

CN 105025787 A 11/2015
CN 105232047 A 1/2016
(Continued)

OTHER PUBLICATIONS

EP 18790656.5 filed Nov. 27, 2019 Supplementary European Search Report dated Apr. 9, 2020.
(Continued)

*Primary Examiner* — Thienvu V Tran
*Assistant Examiner* — Sreeya Sreevatsa
(74) *Attorney, Agent, or Firm* — Rutan & Tucker LLP

(57) ABSTRACT

Disclosed herein are medical-device magnetizer systems and methods. In an example, a magnetizer system can be configured to impart one or more magnetic signatures to a medical device having ferrous elements for medical-device tracking. Such a magnetizer system can include, in some embodiments, a magnetizer. The magnetizer can have an elongate body with a single-dipole section, a multipole section, and a plurality of magnets configured to generate two or more magnetic fields. The single-dipole section can have a magnetizer body defining a cavity having a first magnetic field therein. The multipole section can have a second magnetic field therein. In another example, a method can include imparting a magnetic signature to a plurality of medical devices having ferrous elements using the magnetizer system.

20 Claims, 4 Drawing Sheets

(58) Field of Classification Search
USPC .......................................... 361/143; 600/424
See application file for complete search history.

(56) References Cited

U.S. PATENT DOCUMENTS

| | | | |
|---|---|---|---|
| 3,847,157 A | 11/1974 | Caillouette et al. |
| 4,063,561 A | 12/1977 | McKenna |
| 4,161,943 A | 7/1979 | Nogier |
| 4,237,518 A | 12/1980 | Krulwich |
| 4,458,705 A | 7/1984 | Cawood |
| 4,529,954 A | 7/1985 | Steingroever et al. |
| 4,633,237 A | 12/1986 | Tucknott et al. |
| 5,055,813 A | 10/1991 | Johnson |
| 5,659,279 A | 8/1997 | Janssen et al. |
| 5,803,089 A | 9/1998 | Ferre et al. |
| 5,845,646 A | 12/1998 | Lemelson |
| 6,154,352 A | 11/2000 | Atallah |
| 6,249,199 B1 | 6/2001 | Liu |
| 6,310,532 B1 | 10/2001 | Santa Cruz et al. |
| 6,432,036 B1 | 8/2002 | Kim |
| 7,023,309 B2 | 4/2006 | Laskaris et al. |
| 7,090,639 B2 | 8/2006 | Govari |
| 7,135,978 B2 | 11/2006 | Gisselberg et al. |
| 7,214,191 B2 | 5/2007 | Stringer et al. |
| 7,775,215 B2 | 8/2010 | Hassler, Jr. et al. |
| 7,775,966 B2 | 8/2010 | Dlugos et al. |
| 7,850,006 B2 | 12/2010 | Uchiyama |
| 7,873,401 B2 | 1/2011 | Shachar |
| 7,887,516 B2 | 2/2011 | Young |
| 7,927,270 B2 | 4/2011 | Dlugos et al. |
| 8,016,744 B2 | 9/2011 | Dlugos et al. |
| 8,016,745 B2 | 9/2011 | Hassler, Jr. et al. |
| 8,174,346 B1 | 5/2012 | Koren |
| 8,240,211 B2 | 8/2012 | Zeitner et al. |
| 8,388,541 B2 | 3/2013 | Messerly et al. |
| 8,475,407 B2 | 7/2013 | Kalpin et al. |
| 8,483,802 B2 | 7/2013 | Kalpin et al. |
| 8,532,743 B2 | 9/2013 | Stangenes et al. |
| 8,622,975 B2 | 1/2014 | Andreoni et al. |
| 8,725,435 B2 | 5/2014 | Snow et al. |
| 8,781,555 B2 | 7/2014 | Burnside et al. |
| 8,840,541 B2 | 9/2014 | Snow et al. |
| 8,849,382 B2 | 9/2014 | Cox et al. |
| 8,939,888 B2 | 1/2015 | Augarten et al. |
| 9,017,283 B2 | 4/2015 | Birchard et al. |
| 9,113,812 B2 | 8/2015 | Kalpin et al. |
| 9,155,517 B2 | 10/2015 | Dunbar et al. |
| 9,216,257 B2 | 12/2015 | Kalpin et al. |
| 9,224,529 B2 | 12/2015 | Gery |
| 9,257,220 B2 | 2/2016 | Nicholls et al. |
| 9,299,925 B2 | 3/2016 | Yi et al. |
| 9,308,022 B2 | 4/2016 | Chitre et al. |
| 9,339,601 B2 | 5/2016 | Kalpin et al. |
| 9,439,653 B2 | 9/2016 | Avneri et al. |
| 9,456,766 B2 | 10/2016 | Cox et al. |
| 9,459,087 B2 | 10/2016 | Dunbar et al. |
| 9,492,097 B2 | 11/2016 | Wilkes et al. |
| 9,517,299 B2 | 12/2016 | Tieck et al. |
| 9,521,961 B2 | 12/2016 | Silverstein et al. |
| 9,554,716 B2 | 1/2017 | Burnside et al. |
| 9,597,008 B2 | 3/2017 | Henkel et al. |
| 9,636,031 B2 | 5/2017 | Cox |
| 9,649,048 B2 | 5/2017 | Cox et al. |
| 9,744,291 B2 | 8/2017 | Tieck et al. |
| 10,032,552 B2 | 7/2018 | Ma et al. |
| 10,449,330 B2 | 10/2019 | Newman et al. |
| 10,524,691 B2 | 1/2020 | Newman et al. |
| 10,751,509 B2 | 8/2020 | Misener |
| 11,344,220 B2 | 5/2022 | Burkholz et al. |
| 11,369,410 B2 | 6/2022 | Lindekugel |
| 2003/0040671 A1 | 2/2003 | Somogyi et al. |
| 2003/0052785 A1 | 3/2003 | Gisselberg et al. |
| 2004/0019447 A1 | 1/2004 | Shachar |
| 2004/0051610 A1 | 3/2004 | Sajan |
| 2005/0059884 A1 | 3/2005 | Krag |
| 2006/0114088 A1 | 6/2006 | Shachar |
| 2006/0211914 A1 | 9/2006 | Hassler et al. |
| 2007/0244373 A1 | 10/2007 | Osypka |
| 2007/0290654 A1 | 12/2007 | Govari et al. |
| 2008/0049367 A1* | 2/2008 | Carson ............... H02H 3/12 361/87 |
| 2008/0146939 A1 | 6/2008 | McMorrow et al. |
| 2010/0043561 A1 | 2/2010 | Zeitner et al. |
| 2010/0096553 A1 | 4/2010 | Patil et al. |
| 2010/0210950 A1 | 8/2010 | Dunbar et al. |
| 2011/0060185 A1 | 3/2011 | Ikuma et al. |
| 2011/0196235 A1 | 8/2011 | Dunbar et al. |
| 2011/0237936 A1 | 9/2011 | Kalpin et al. |
| 2011/0237937 A1 | 9/2011 | Kalpin et al. |
| 2013/0150714 A1 | 6/2013 | Howlett et al. |
| 2013/0296691 A1 | 11/2013 | Ashe |
| 2014/0031674 A1 | 1/2014 | Newman et al. |
| 2014/0165796 A1 | 6/2014 | Gauthier et al. |
| 2014/0253270 A1 | 9/2014 | Nicholls et al. |
| 2014/0257080 A1 | 9/2014 | Dunbar et al. |
| 2014/0257104 A1 | 9/2014 | Dunbar et al. |
| 2014/0257746 A1 | 9/2014 | Dunbar et al. |
| 2015/0080710 A1 | 3/2015 | Henkel et al. |
| 2015/0359991 A1 | 12/2015 | Dunbar et al. |
| 2015/0365787 A1 | 12/2015 | Farrell |
| 2016/0015472 A1 | 1/2016 | Tiernan et al. |
| 2016/0351312 A1 | 12/2016 | Koren |
| 2017/0007200 A1 | 1/2017 | Hagy et al. |
| 2017/0079548 A1 | 3/2017 | Silverstein et al. |
| 2017/0079549 A1 | 3/2017 | Henkel et al. |
| 2017/0079550 A1 | 3/2017 | Henkel et al. |
| 2017/0079551 A1 | 3/2017 | Henkel et al. |
| 2017/0126864 A1 | 5/2017 | Lim et al. |
| 2017/0261564 A1 | 9/2017 | Gabrys et al. |
| 2017/0325713 A1 | 11/2017 | Burkholz et al. |
| 2017/0326342 A1 | 11/2017 | Ma et al. |
| 2018/0061546 A1 | 3/2018 | Ma et al. |
| 2018/0289929 A1* | 10/2018 | Ma ................... A61M 25/0127 |
| 2018/0310955 A1* | 11/2018 | Lindekugel ............ A61B 90/11 |
| 2019/0298221 A1 | 10/2019 | Sonderegger |
| 2020/0360662 A1 | 11/2020 | Ma et al. |
| 2021/0065857 A1 | 3/2021 | Newman et al. |
| 2021/0169585 A1* | 6/2021 | Prince ................. A61B 8/0841 |
| 2022/0105324 A1 | 4/2022 | Broniec et al. |
| 2022/0142501 A1 | 5/2022 | Prince et al. |
| 2022/0142502 A1 | 5/2022 | Prince et al. |
| 2022/0323101 A1 | 10/2022 | Lindekugel et al. |
| 2022/0401158 A1* | 12/2022 | Sowards ............... A61B 34/20 |
| 2024/0090793 A1 | 3/2024 | Prince et al. |

FOREIGN PATENT DOCUMENTS

| | | |
|---|---|---|
| CN | 103945772 B | 9/2016 |
| CN | 105073067 B | 6/2017 |
| DE | 102006033229 B4 | 5/2013 |
| EP | 2015105 B1 | 6/2011 |
| EP | 2730306 A1 | 5/2014 |
| EP | 2285287 B1 | 4/2015 |
| EP | 2939599 A2 | 11/2015 |
| EP | 2939601 A2 | 11/2015 |
| EP | 2997901 A1 | 3/2016 |
| EP | 2753243 B1 | 4/2016 |
| JP | 5349582 B2 | 11/2013 |
| JP | 5908981 B2 | 4/2016 |
| JP | 6242421 B2 | 12/2017 |
| KR | 20150123233 A | 11/2015 |
| WO | 2008009442 A2 | 1/2008 |
| WO | 2009010386 A1 | 1/2009 |
| WO | 2009129845 A1 | 10/2009 |
| WO | 2013034175 A1 | 3/2013 |
| WO | 2013142386 A1 | 9/2013 |
| WO | 2014062728 A1 | 4/2014 |
| WO | 2014135592 A1 | 9/2014 |
| WO | 16096190 A1 | 6/2016 |
| WO | 17016961 A1 | 2/2017 |
| WO | 2018/201053 A1 | 11/2018 |
| WO | 2022/099147 A1 | 5/2022 |

(56) References Cited

FOREIGN PATENT DOCUMENTS

| WO | 2022103772 A1 | 5/2022 |
|---|---|---|
| WO | 2022271864 A1 | 12/2022 |
| WO | 2023009446 A1 | 2/2023 |

OTHER PUBLICATIONS

EP 221711096 filed May 2, 2022, Extended European Search Report dated Jul. 22, 2022.
EP20202521.9 filed Oct. 19, 2020 Extended European Search Report dated Jan. 28, 2021.
PCT/US2018/029958 filed Apr. 27, 2018 Communication Pursuant to Rules 70(2) and 70a(2) dated Apr. 29, 2020.
PCT/US2018/029958 filed Apr. 27, 2018 International Search Report and Written Opinion dated Jul. 11, 2018.
PCT/US2018/029958 filed Apr. 27, 2018 International Search Report dated Apr. 27, 2018.
PCT/US2021/058478 filed Nov. 8, 2021 International Search Report and Written Opinion dated Mar. 1, 2022.
U.S. Appl. No. 15/965,419, filed Apr. 27, 2018 Final Office Action dated Jan. 15, 2021.
U.S. Appl. No. 15/965,419, filed Apr. 27, 2018 Non-Final Office Action dated Aug. 6, 2021.
U.S. Appl. No. 15/965,419, filed Apr. 27, 2018 Non-Final Office Action dated Sep. 24, 2020.
U.S. Appl. No. 15/965,419, filed Apr. 27, 2018 Notice of Allowance dated Feb. 16, 2022.
PCT/US2022/034584 filed Jun. 22, 2022, International Search Report and Written Opinion dated Oct. 10, 2022.
PCT/US2022/038202 filed Jul. 25, 2022 International Search Report and Written Opinion dated Nov. 14, 2022.
PCT/US2021/058667 filed Nov. 9, 2021 International Search Report and Written Opinion dated Mar. 1, 2022.
PCT/US2022/034584 filed Jun. 22, 2022, International Preliminary Report on Patentability dated Dec. 14, 2023.
U.S. Appl. No. 17/521,680, filed Nov. 8, 2021 Non-Final Office Action dated Jun. 2, 2023.
U.S. Appl. No. 17/521,680, filed Nov. 8, 2021 Notice of Allowance dated Oct. 11, 2023.
U.S. Appl. No. 17/522,828, filed Nov. 9, 2021 Non-Final Office Action dated Nov. 9, 2023.
U.S. Appl. No. 17/850,468, filed Jun. 27, 2022 Restriction Requirement dated Dec. 29, 2023.
U.S. Appl. No. 17/522,828, filed Nov. 9, 2021 Notice of Allowance dated Apr. 3, 2024.
U.S. Appl. No. 17/846,973, filed Jun. 22, 2022 Non-Final Office Action dated Jun. 12, 2024.
U.S. Appl. No. 18/524,659, filed Nov. 30, 2023 Non-Final Office Action dated Jul. 29, 2024.
U.S. Appl. No. 17/846,973, filed Jun. 22, 2022 Notice of Allowance dated Oct. 31, 2024.
U.S. Appl. No. 17/850,468, filed Jun. 27, 2022 Notice of Allowance dated Sep. 5, 2024.
U.S. Appl. No. 18/524,659, filed Nov. 30, 2023 Notice of Allowance dated Nov. 21, 2024.

* cited by examiner

MEDICAL-DEVICE MAGNETIZER SYSTEMS AND METHODS

PRIORITY

This application claims the benefit of priority to U.S. Provisional Patent Application No. 63/225,793, filed Jul. 26, 2021, which is incorporated by reference in its entirety into this application.

BACKGROUND

A ferrous medical device can be magnetized for the purpose of tracking the ferrous medical device in 3-dimensional ("3D") space. The ferrous medical device can be brought into a magnetic field of a magnetizer, thereby imparting to the medical device a unique magnetic signature able to be tracked in 3D space. However, if multiple unique magnetic signatures are needed, multiple different magnetizers are required. It would be beneficial to have one magnetizer configured to provide multiple unique magnetic signatures.

Disclosed herein are medical-device magnetizer systems and methods that address the foregoing.

SUMMARY

Disclosed herein is a magnetizer system configured to impart one or more magnetic signatures to a medical device having ferrous elements for medical-device tracking. The magnetizer system includes, in some embodiments, a magnetizer. The magnetizer has an elongate body with a single-dipole section, a multipole section, and a plurality of magnets configured to generate two or more magnetic fields. The single-dipole section has a magnetizer body defining a cavity configured to have a first magnetic field therein. The multipole section is configured to have a second magnetic field therein.

In some embodiments, the magnetizer includes one or more sensors configured to detect the medical device through optical sensing, inductive sensing, or a radiofrequency identification ("RFID") reader configured to detect an RFID tag coupled to the medical device.

In some embodiments, the one-or-more sensors are configured to be in communication with a computing device or another medical device.

In some embodiments, the one-or-more sensors are configured to communicate the imparting of the one-or-more magnetic signatures to the medical device, the computing device, or the other medical device.

In some embodiments, the other medical device is an ultrasound probe.

In some embodiments, the first magnetic field is configured to impart a single-dipole magnetic signature. The second magnetic field is configured to impart a multipole magnetic signature.

In some embodiments, the multipole section includes two shoulders extending perpendicularly from the elongate body. The two shoulders define a trough configured to receive the medical device therein.

In some embodiments, the plurality of magnets are configured to impart the single-dipole magnetic signature within the cavity and the multipole magnetic signature within the trough.

In some embodiments, one or more magnets of the plurality of magnets are configured to impart the single-dipole magnetic signature within the cavity. One or more other magnets of the plurality of magnets are configured to impart the multipole magnetic signature within the trough.

In some embodiments, the one-or-more magnets of the plurality of magnets are located within the cavity.

In some embodiments, the one-or-more other magnets of the plurality of magnets are arranged in an array of magnets within the trough.

In some embodiments, one or both of the shoulders include a post extending therefrom. Each post is configured to guide a tray having the medical device in a horizontal orientation thereon into the trough.

In some embodiments, the tray having the medical device in the horizontal orientation thereon is configured to be lowered vertically into the trough and subsequently removed to impart the multipole magnetic signature to the medical device.

In some embodiments, the magnetizer is configured for the medical device to be slidably inserted into the cavity in a horizontal orientation and subsequently withdrawn from the cavity to impart the single-dipole magnetic signature to the medical device.

In some embodiments, the magnetizer is configured for the medical device to be slidably inserted into the cavity in a vertical orientation and subsequently withdrawn from the cavity to impart the single-dipole magnetic signature to the medical device.

In some embodiments, the single-dipole section and the multipole section are on opposite ends of the magnetizer.

In some embodiments, the single-dipole section and the multipole section are alongside each other in the magnetizer.

In some embodiments, the plurality of magnets include electromagnets.

In some embodiments, the magnetizer includes a mechanical switch configured to detect the medical device.

In some embodiments, the mechanical switch is configured to indicate whether the medical device includes any magnetic signature thereon.

Also disclosed herein is a method of imparting a magnetic signature to a plurality of medical devices having ferrous elements using a magnetizer system. The method includes, in some embodiments, slidably inserting a first medical device into a single-dipole section of a magnetizer body of a magnetizer to impart a single-dipole magnetic signature to the ferrous elements of the first medical device with a first magnetic field; placing a second medical device in a horizontal orientation in a multipole section of the magnetizer to impart a multipole magnetic signature to the ferrous elements of the second medical device with a second magnetic field; and removing the first and second medical devices from the magnetizer.

In some embodiments, slidably inserting the first medical device into the single-dipole section of the magnetizer body includes slidably inserting the first medical device in the horizontal orientation or a vertical orientation.

In some embodiments, the magnetizer body defines a cavity having one or more magnets of a plurality of magnets therein. The one-or-more magnets are configured to generate the first magnetic field.

In some embodiments, the multipole section of the magnetizer includes one or more other magnets of the plurality of magnets. The one-or-more other magnets are configured to generate the second magnetic field.

In some embodiments, the multipole section of the magnetizer includes two shoulders extending perpendicularly from the magnetizer. The two shoulders have the one-ormore other magnets of the plurality of magnets therein. The two shoulders also define a trough including the second magnetic field therein.

In some embodiments, placing the second medical device in the horizontal orientation in the multipole section of the magnetizer includes lowering the second medical device on a tray into the trough.

In some embodiments, removing the second medical device from the magnetizer includes removing the second medical device from the magnetizer in the vertical orientation from the multipole section by removing the tray from the trough.

In some embodiments, removing the first medical device from the magnetizer includes slidably removing the first medical device in the horizontal orientation from a cavity defined by the magnetizer body.

In some embodiments, removing the medical device from the magnetizer includes slidably removing the first medical device from the magnetizer in a vertical orientation from a cavity defined by the magnetizer body.

In some embodiments, removing the second medical device from the magnetizer includes withdrawing the second medical device from the magnetizer in the horizontal orientation from the multipole section of the magnetizer.

These and other features of the concepts provided herein will become more apparent to those of skill in the art in view of the accompanying drawings and following description, which describe particular embodiments of such concepts in greater detail.

DRAWINGS

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The term "computing device" should be construed as electronics with the data processing capability and/or a capability of connecting to any type of network, such as a public network (e.g., Internet), a private network (e.g., a wireless data telecommunication network, a local area network ["LAN"], etc.), or a combination of networks. Examples of a computing device can include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

Unless defined otherwise, all technical and scientific terms used herein have the same meaning as commonly understood by those of ordinary skill in the art.

Figure 1:
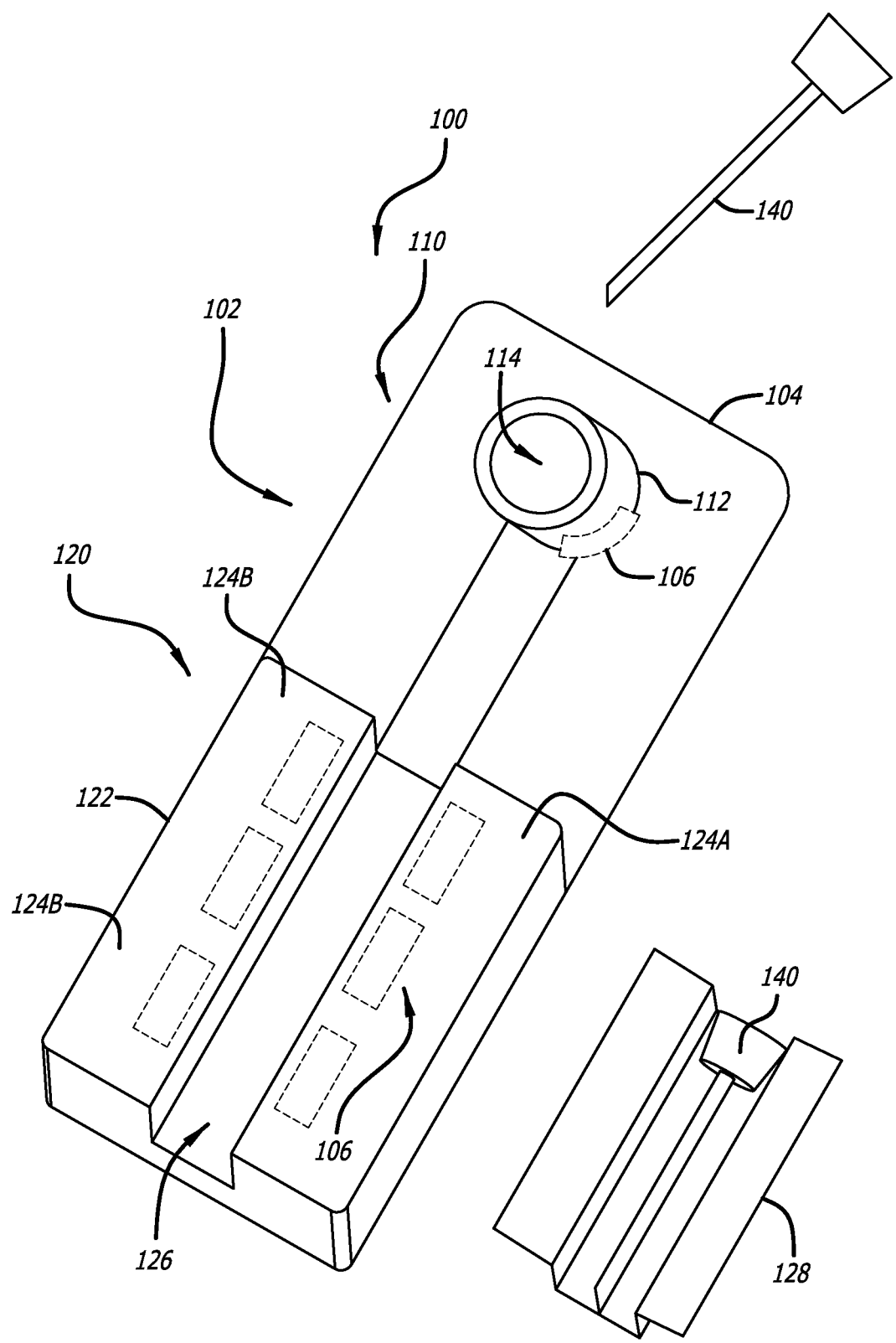
FIG. 1 illustrates a perspective view of a magnetizer, in accordance with some embodiments.

FIG. 1 illustrates a perspective view of a magnetizer system 100, in accordance with some embodiments. In some embodiments, the magnetizer system 100 includes a magnetizer 102 having an elongate magnetizer body 104 having a single-dipole section 110 and a multipole section 120. Each section is configured to include a magnetic field that imparts a unique magnetic signature on ferrous elements of a medical device 140 within the magnetic field for medical-device tracking. In some embodiments, the single-dipole section 110 and the multipole section 120 can each include a plurality of magnets 106 arranged in a configuration such as an array. In some embodiments, the plurality of magnets 106 can be shared between the single-dipole section 110 and the multipole section 120. The medical device 140 having the ferrous elements can be configured to be brought into the magnetic field to have the unique magnetic signature imparted thereto for medical-device tracking in 3D space.

Figure 2:
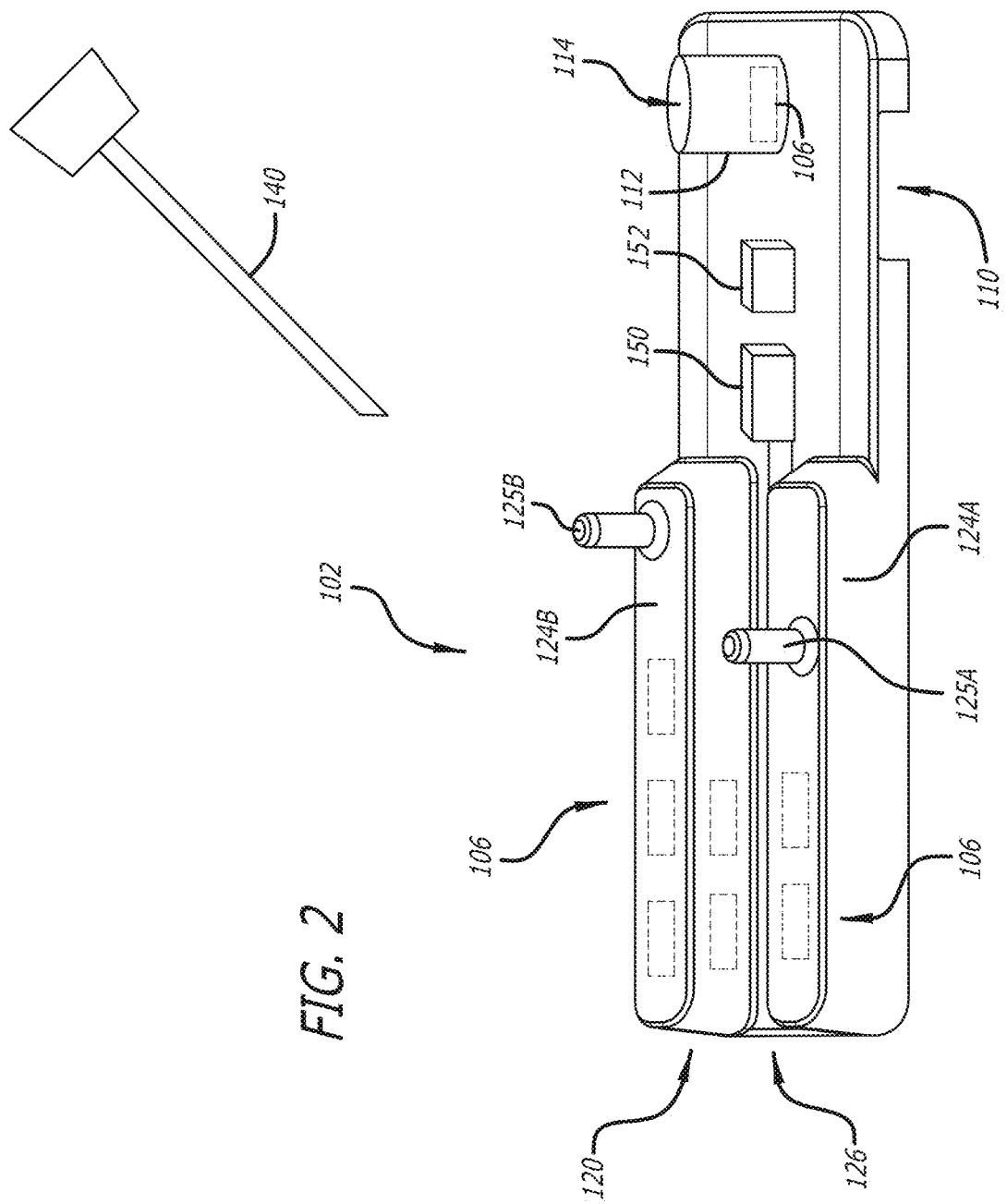
FIG. 2 illustrates a side view of the magnetizer, in accordance with some embodiments.

In some embodiments, the single-dipole section 110 can include a single dipole magnetizer 112 having the magnetizer body 104 configured as a magnetizer body that defines a cavity 114 such as tube extending from a surface of the magnetizer body 104 or into a shoulder of the shoulders 124A and 124B. In some embodiments, the single dipole magnetizer 112 can extend perpendicularly from the magnetizer body 104 as shown in FIG. 2. In some embodiments, the magnetizer body 104 can include one or more magnets from the plurality of magnets 106 therein configured to generate a magnetic field within the cavity 114. In some embodiments, the magnetic field within the cavity 114 can be configured to impart a single-dipole magnetic signature to ferrous elements therein. In some embodiments, the single dipole magnetizer 112 can be detachably coupled to the magnetizer body 104 through a press fit, a snap fit, an interference fit, or the like.

The multipole section 120 can include a multipole magnetizer 122, extending perpendicular from the magnetizer 102. In some embodiments, the multipole magnetizer 122 can include two elongated shoulders 124A and 124B extending perpendicularly from the magnetizer 102 (e.g., longitudinal walls of the shoulders 124A and 124B are perpendicular to a surface of the magnetizer 102), thereby defining a trough 126 along a central portion of a length of the magnetizer 102. In some embodiments, the trough 126 can be configured to receive a tray 128 therein. The tray 128 can include the medical device 140 having ferrous elements therein, allowing the user the ability to easily place the medical device 140 into and remove the medical device 140 from a multipole magnetic field. In some embodiments, one or more magnets of the plurality of magnets 106 can reside within the shoulders 124A and 124B, within the trough 126, or both, and the one-or-more magnets of the plurality of magnets 106 can generate the multipole magnetic field within the trough 126. Advantageously, the magnetizer 102 can be used to impart either a single-dipole magnetic signature or a multipole magnetic signature to the medical device 140 having ferrous elements instead of having multiple separate magnetizers to impart either the single-dipole magnetic signature or the multipole magnetic signature to allow for unique tracking depths and packaging configurations of the medical device 140.

FIG. 2 illustrates a side view of the magnetizer 102, in accordance with some embodiments. In some embodiments, the magnetizer 102 can be configured to detect the magnetic signature of the medical device 140. In some embodiments, the magnetizer 102 can include one or more sensors 150 configured to detect the presence of the medical device 140 or the magnetic signature of the medical device 140. In some embodiments, the one-or-more sensors 150 can be configured to be in communication with a computing device or another medical device. In some embodiments, the one-or-more sensors 150 can be in wireless communication with the computing device or the other medical device. Example wireless communication modalities can include Wi-Fi, Bluetooth, Near Field Communications ("NFC"), cellular Global System for Mobile Communication ("GSM"), electromagnetic ("EM"), radiofrequency ("RF"), combinations thereof, or the like. In some embodiments, the one-or-more sensors 150 can be configured to detect the status of imparting the one-or-more magnetic signatures to the medical device 140, wherein the status of imparting the one-or-more magnetic signatures to the medical device 140 can range from pending, initiating, currently imparting, and finished imparting. In such embodiments, the one-or-more sensors 150 can be further configured to communicate to the computing device or the other medical device the status of the imparting of the one-or-more magnetic signatures to the medical device 140. In some embodiments, the other medical device can include an ultrasound probe or the like. In some embodiments, the one-or-more sensors 150 can include one or more of: a RFID reader configured to detect a RFID tag coupled to the medical device 140, an optical sensor, or an inductive sensor. In some embodiments, the one-or-more sensors 150 can be in communication with a console, the console being in wireless communication with a computing device or another medical device. In some embodiments, the one-or-more sensors 150 can be coupled to the magnetizer 102, can be embedded within the magnetizer 102 or formed integrally into the magnetizer 102. In some embodiments, the magnetizer 102 can include a mechanical switch 152 configured to detect the presence of the medical device 140 or indicate that the medical device 140 includes a magnetic signature thereon.

In some embodiments, the plurality of magnets 106 can include passive magnets or active magnets (e.g., electromagnets). In some embodiments, the multipole section 120 can be configured to receive therein the medical device 140.

In some embodiments, the multipole section 120 have include one or more posts 125A, 125B, . . . , 125n extending transversely or perpendicularly from the shoulders 124A and 124B. The one-or-more posts 125A, 125B, . . . , 125n can be configured to guide the tray 128 holding the medical device 140 therein into the trough 126, allowing the tray 128 to be precisely lowered and removed from the trough 126 vertically to ensure the unique multipole magnetic signature is imparted to the medical device 140.

In some embodiments, the single-dipole section 110 can be located opposite the multipole section 120 such as on opposite ends of the magnetizer 102. In some embodiments, the single dipole magnetizer 112 can extend transversely from the magnetizer 102. In some embodiments, the single dipole magnetizer 112 can be shaped in a tube or cylinder, a right prism such as a rectangular prism, or the like, thereby defining the cavity 114. The cavity 114 can include therein one or more magnets of the plurality of magnets 106, wherein the medical device 140, in a vertical orientation, can be slidably inserted into the cavity 114 and removed, to impart the single-dipole magnetic signature to the medical device 140. In some embodiments, the vertical orientation includes where the medical device 140 is perpendicular to the magnetizer 102 or when the single dipole magnetizer 112 extends perpendicularly from the magnetizer 102, the vertical orientation includes when the medical device 140 is parallel to the single dipole magnetizer 112.

Figure 3A:
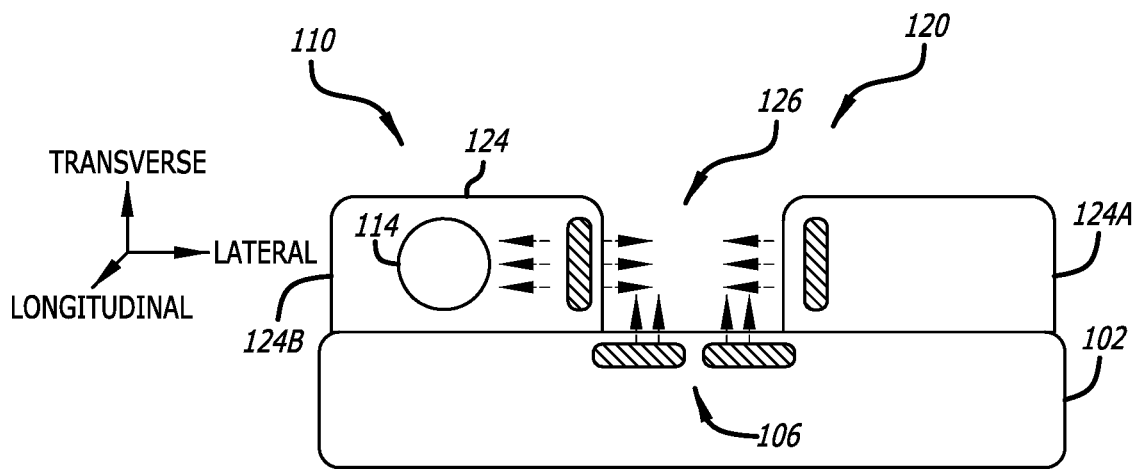
FIG. 3A illustrates a cross sectional view of the magnetizer, in accordance with some embodiments.

FIG. 3A illustrates a cross sectional view of the magnetizer 102, in accordance with some embodiments. In an embodiment, the magnetizer 102 can include the trough 126. In this embodiment, the single-dipole section 110 and the multipole section 120 are alongside each other in the magnetizer 102, allowing the plurality of magnets 106 to generate both the single dipole magnetic field and the multipole magnetic field. The plurality of magnets 106 surround the trough 126 as illustrated in FIG. 3A and generate a multipole magnetic field within the trough 126. The plurality of magnets 106 can be configured to magnetize a portion of the medical device 140 by providing a multipole magnetization. In this embodiment, the magnetizer cavity 114 of the single dipole magnetizer 112 is defined as the tube or cylinder, the right prism such as the rectangular prism, or the like, in one shoulder of the shoulders 124A and 124B, wherein some of the plurality of magnets 106 generate a single dipole magnetic field within the cavity 114. In this embodiment, the cavity 114 can stretch along a portion up to an entirety of the shoulder 124A or 124B.

Figure 3B:
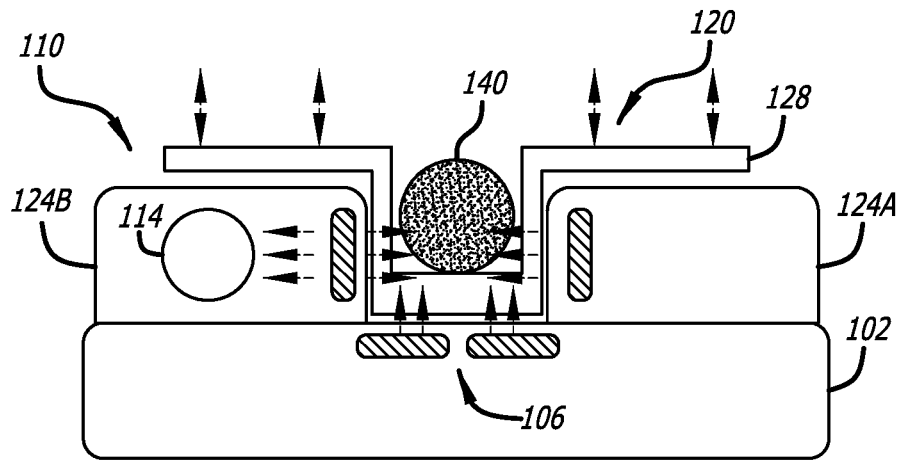
FIG. 3B illustrates a cross sectional view of imparting a multipole magnetic signature or a single-dipole magnetic signature to the medical device, in accordance with some embodiments.
Figure 3C:
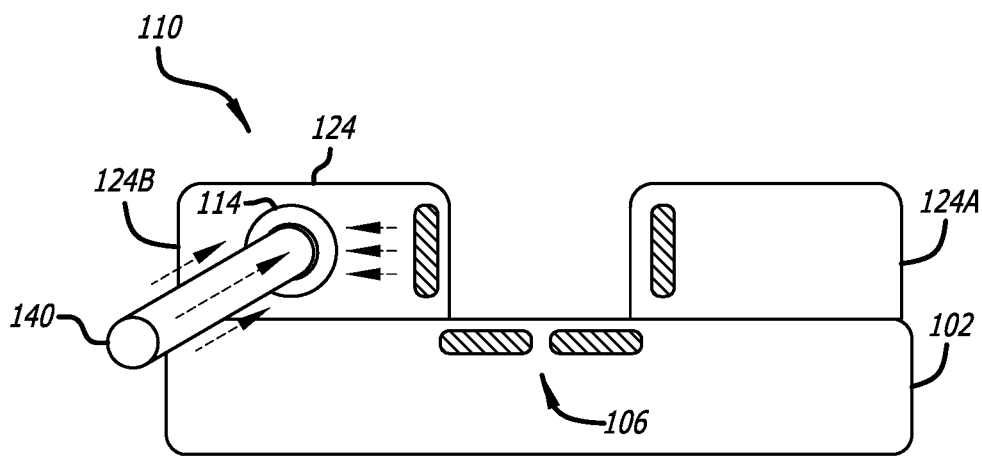
FIG. 3C illustrates a cross sectional view of imparting a multipole magnetic signature or a single-dipole magnetic signature to the medical device, in accordance with some embodiments.

FIGS. 3B and 3C illustrate a cross sectional view of magnetizing the medical device 140 with either a single dipole magnetization or a multipole magnetization, in accordance to some embodiments. In this embodiment, the medical device 140 can be placed in the tray 128 in the trough 126. The plurality of magnets 106 can be configured around the trough 126 so that the plurality of magnets 106 generates a multipole magnetic field therein. The medical device 140 in a horizontal orientation within the tray 128 can be lowered into the trough 126 wherein the multipole magnetic field magnetizes a portion of the medical device 140 with a multipole magnetic signature. In some embodiments, the horizontal orientation includes when the medical device 140 is parallel to the magnetizer 102. The tray 128 containing the medical device 140 can be removed from the trough 126 by lifting vertically while the medical device 140 is in the horizontal configuration. The medical device 140 having the magnetic signature thereon can then be tracked in 3D space by various means.

As illustrated in FIG. 3C, the magnetizer 102 includes the trough 126 and further includes the cavity 114. The cavity 114 can be located longitudinally in line with one or more magnets of the plurality of magnets 106. The plurality of magnets 106 can be configured to generate a single dipole magnetic field within the cavity 114. The plurality of magnets 106 can be configured to generate a single dipole magnetic field along at least a portion of the length of the cavity 114. The medical device 140 in a horizontal orientation can be inserted longitudinally into the cavity 114 and slidably removed from the cavity 114. As the medical device 140 is slidably removed from the cavity 114, the single dipole magnetic field imparts a single-dipole magnetic signature to a portion of the medical device 140.

Notably, the magnetic signature can be consistent an encoding of differentiating information or data for the medical device 140 such that the magnetic signature of a first instance of the medical device 140 is different from that of a second instance of the medical device 140. In some embodiments, the differentiating information or data can include model information for the medical device 140 such as a model name or number of the medical device 140. In some embodiments, the differentiating information or data can include dimensional information for the medical device 140 such as a length or diameter of the medical device 140. In some embodiments, the differentiating information or data can include manufacturing information for the medical device 140 such as a manufacturing date or lot number of the medical device 140. In some embodiments, the differentiating information or data can include unique information pertaining to the medical device 140 such as a serial number of the medical device 140. As such, in some embodiments, the magnetic signature for each instance of the medical device 140 can be unique with respect to that for every other instance of the medical device 140.

Figure 4:
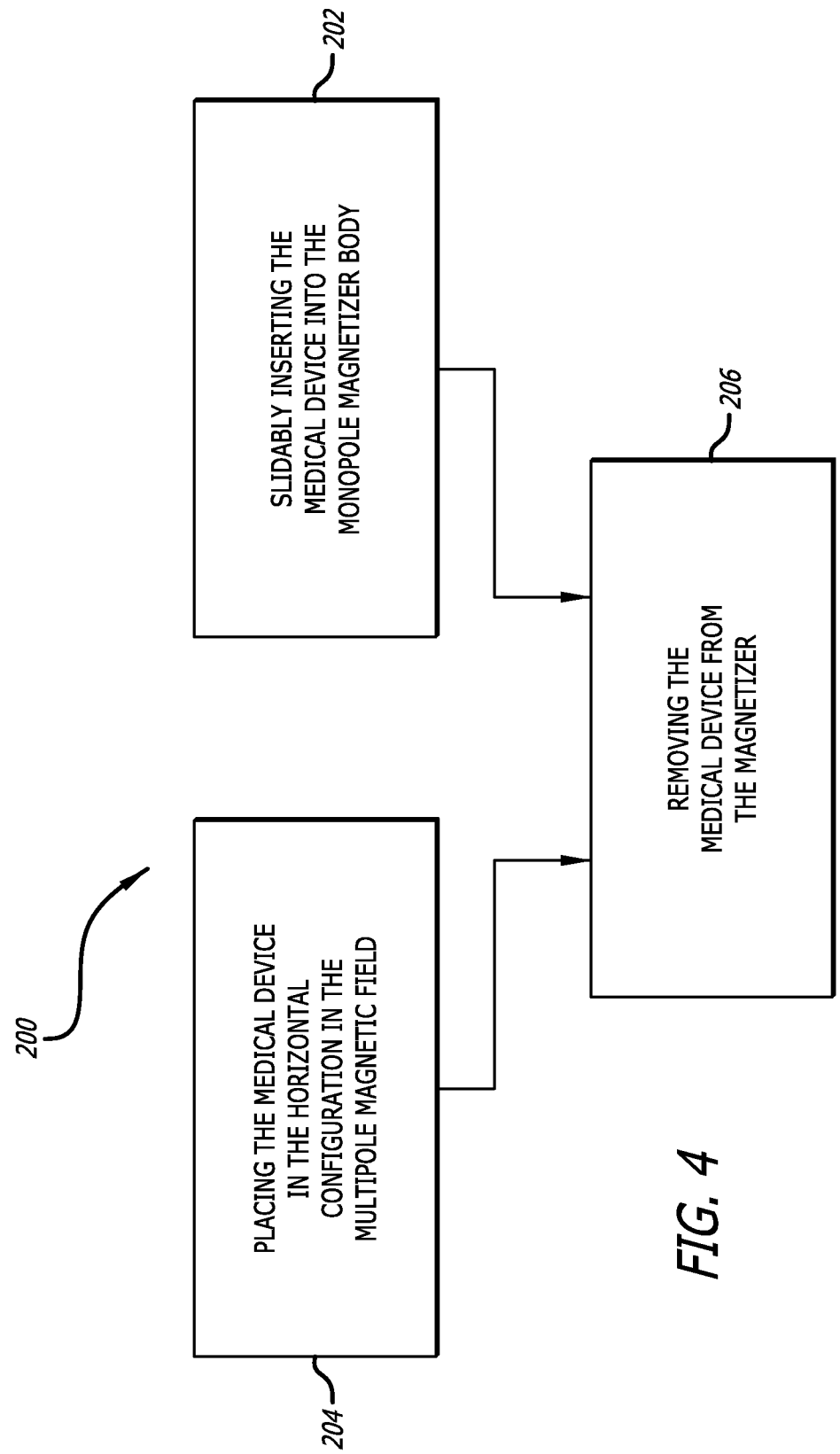
FIG. 4 illustrates a flow chart of a method of imparting a multipole magnetic signature or a single dipole signature to the medical device, in accordance with some embodiments.

FIG. 4 illustrates a flow chart of a method 200 of imparting a magnetic signature to the medical device 140 or a plurality of such medical devices having ferrous elements, in accordance with some embodiments. In some embodiments, the method 200 further includes slidably inserting the medical device 140 or a first medical device of the plurality of medical devices in the single dipole magnetizer 112 to impart a single-dipole magnetic signature (block 202). In some embodiments, the single dipole magnetizer 112 includes the cavity 114 and one or more of the plurality of magnets 106 therein. In some embodiments, slidably inserting the medical device 140 or the first medical device of the plurality of medical devices into the single dipole magnetizer 112 includes slidably inserting it into the single dipole magnetizer 112 in the vertical orientation or the horizontal orientation.

In some embodiments, the method 200 further includes placing the medical device 140 or a second medical device of the plurality of medical devices in the horizontal orientation in the multipole magnetic field to impart a multipole magnetic signature (block 204). In some embodiments, placing the medical device 140 or the second medical device of the plurality of medical devices in the horizontal orientation in the multipole magnetic field includes lowering it into the trough 126. Other methods of placing the medical device 140 or the second medical device of the plurality of medical devices in the horizontal orientation in the multipole magnetic field are considered. In some embodiments, placing the medical device 140 or the second medical device of the plurality of medical devices in the horizontal orientation in the multipole magnetic field includes lowering it on the tray 128 into the trough 126.

The method 200 further includes removing the medical device 140 or the first and second medical devices of the plurality of medical devices from the magnetizer system 100 (block 206). In some embodiments, removing the medical device 140 or the first medical device of the plurality of medical devices from the magnetizer system 100 includes slidably removing it in the horizontal orientation or the vertical orientation from the cavity 114 of the single dipole magnetizer 112. In some embodiments, removing the medical device 140 or the second medical device of the plurality of medical devices from the magnetizer system 100 includes withdrawing it in the horizontal orientation from the multipole magnetic field. In some embodiments, withdrawing the medical device 140 or the second medical device of the plurality of medical devices in the horizontal orientation from the multipole magnetic field includes removing the tray 128 from the trough 126.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures can be made from the particular embodiments disclosed herein without departing from the scope of the concepts provided herein.

What is claimed is:

1. A magnetizer system configured to impart one or more magnetic signatures to a medical device having ferrous elements for medical-device tracking, comprising:
    a magnetizer having an elongate body defining a longitudinal axis and comprising:
        a single-dipole section having a cavity defining a central axis extending parallel to the longitudinal axis and configured to receive a first medical device along the central axis;
        a multipole section having a trough extending parallel to the central axis of the single-dipole section and configured to receive a second medical device perpendicular to the longitudinal axis; and
        a first magnetic element disposed within the elongate body of the magnetizer and between the central axis of the single-dipole section and the trough of the multipole section, the first magnetic element imparting a first magnetic signature on the first medical device or a second magnetic signature on the second medical device.

2. The magnetizer system according to claim 1, wherein the magnetizer includes one or more sensors configured to detect the medical device through optical sensing, inductive sensing, or a radiofrequency identification ("RFID") reader configured to detect an RFID tag coupled to the medical device.

3. The magnetizer system according to claim 2, wherein the one or more sensors are configured to be in communication with a computing device or a third medical device.

4. The magnetizer system according to claim 3, wherein the one or more sensors are configured to communicate imparting the first magnetic signature or the second magnetic signature to one or more of the first medical device, the second medical device, the computing device, or the third medical device.

5. The magnetizer system according to claim 3, wherein the third medical device is an ultrasound probe.

6. The magnetizer system according to claim 1, wherein the first magnetic signature is configured to impart a single-dipole magnetic signature, and the second magnetic signature is configured to impart a multipole magnetic signature.

7. The magnetizer system according to claim 6, wherein the multipole section includes a first shoulder and a second shoulder extending perpendicularly from the elongate body, the first shoulder and the second shoulder defining the trough configured to receive the second medical device therein.

8. The magnetizer system according to claim 7, further including a plurality of magnets configured to impart one or both of the first magnetic signature within the cavity and the second magnetic signature within the trough.

9. The magnetizer system according to claim 8, wherein the plurality of magnets are disposed within the elongate body of the magnetizer adjacent a sidewall or a bottom surface of the trough.

10. The magnetizer system according to claim 7, wherein one or both of the first shoulder and the second shoulder includes a post extending transversely therefrom, each post configured to guide a tray having the second medical device therein into the trough along a transverse axis.

11. The magnetizer system according to claim 10, wherein an axis of the second medical device disposed in the tray that is engaged with the trough is aligned parallel with the longitudinal axis of the elongate body of the magnetizer.

12. The magnetizer system according to claim 1, wherein the first magnetic element is an electromagnet.

13. The magnetizer system according to claim 1, wherein the first magnetic element is a permanent magnet.

14. The magnetizer system according to claim 1, wherein the cavity of the single-dipole section is configured to slidably receive the first medical device into the cavity and subsequently withdraw from the cavity along the longitudinal axis to impart the first magnetic signature to the first medical device.

15. The magnetizer system according to claim 1, wherein the magnetizer includes a mechanical switch configured to detect the medical device.

16. The magnetizer system according to claim 15, further including one or more sensors configured to indicate whether the medical device includes a magnetic signature thereon.

17. The magnetizer system according to claim 1, wherein the first magnetic signature is different from the second magnetic signature.

18. A method of magnetizing one or more medical devices, comprising:
   providing a magnetizer having a body defining a longitudinal axis and comprising:
      a single-dipole section having a cavity defining a central axis extending parallel to the longitudinal axis;
      a multipole section having a trough extending parallel to the central axis of the single-dipole section; and
      a first magnetic element disposed within the body and disposed between the single-dipole section and the multipole section;
   inserting a first medical device into the cavity parallel to the longitudinal axis to impart a first magnetic signature thereon; and
   inserting a second medical device into the trough perpendicular to the longitudinal axis to impart a second magnetic signature thereon.

19. The method according to claim 18, wherein the first magnetic element imparts one or both of the first magnetic signature on the first medical device and the second magnetic signature on the second medical device.

20. The method according to claim 18, further including a second magnetic element disposed in the body and adjacent a bottom surface or a side surface of the trough to impart the second magnetic signature on the second medical device.

* * * * *